United States Patent [19]

Berger et al.

[11] 4,007,176

[45] Feb. 8, 1977

[54] CEPHALOSPORIN DERIVATIVES

[75] Inventors: Christian Berger, Le Plessis Robinson; Daniel Farge, Thiais; Georges Gros, Bourg-la-Reine; Mayer Naoum Messer, Bievres; Claude Moutonnier, Le Plessis-Robinson, all of France

[73] Assignee: Rhone-Poulenc S.A., Paris, France

[22] Filed: Nov. 12, 1974

[21] Appl. No.: 523,007

[30] Foreign Application Priority Data

Nov. 14, 1973 France .............................. 73.40431
Apr. 25, 1974 France .............................. 74.14436

[52] U.S. Cl. .......................... 260/243 C; 424/246
[51] Int. Cl.² ...................................... C07D 501/24
[58] Field of Search ............................. 260/243 C

[56] References Cited

UNITED STATES PATENTS

| | | | |
|---|---|---|---|
| 3,516,997 | 6/1970 | Takano et al. | 260/243 C |
| 3,692,779 | 9/1972 | Huldrege | 260/243 C |
| 3,886,151 | 5/1975 | Wei | 260/243 C |

*Primary Examiner*—Nicholas S. Rizzo
*Attorney, Agent, or Firm*—Stevens, Davis, Miller & Mosher

[57] ABSTRACT

New cephalosporin derivatives of the formula:

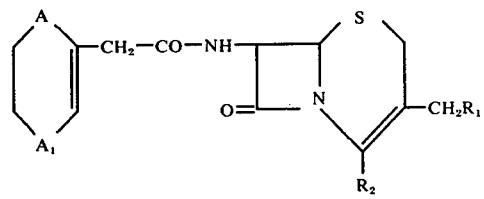

wherein one of A and $A_1$ represents oxygen or sulphur and the other represents sulphur, $R_1$ represents hydrogen, acetoxy, (5-methyl-1,3,4-thiadiazol-2-yl)thio or (1-methyl-1,2,3,4-tetrazol-5-yl)thio and $R_2$ represents carboxy, or $R_1$ represents a pyridinio radical and $R_2$ represents the carboxylate ion, are therapeutically useful compounds possessing antibacterial properties.

12 Claims, No Drawings

CEPHALOSPORIN DERIVATIVES

This invention relates to new therapeutically useful cephalosporin derivatives, to processes for their preparation, and pharmaceutical compositions containing them.

The cephalosporin derivatives of the present invention are those compounds of the general formula:

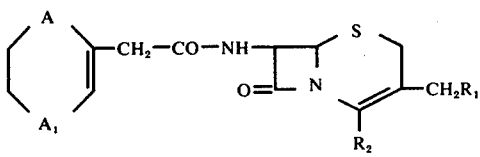

wherein one of the symbols A and $A_1$ represents an oxygen or sulphur atom and the other represents a sulphur atom, the symbol $R_1$ represents a hydrogen atom or an acetoxy, (5-methyl-1,3,4-thiadiazol-2-yl)thio or (1-methyl-1,2,3,4-tetrazol-5-yl)thio radical and the symbol $R_2$ represents the carboxy radical, or alternatively $R_1$ represents a pyridinio radical and $R_2$ represents the carboxylate ion ($-COO^-$), and when $R_2$ represents the carboxy radical salts thereof, for example alkali metal, alkaline earth metal, ammonium and amine salts.

According to a feature of the invention, the cephalosporin derivatives of general formula I are prepared by the process which comprises reacting an acetic acid derivative of the general formula:

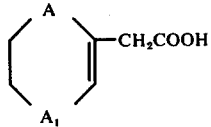

(wherein A and $A_1$ are as hereinbefore defined), or of a derivative of the acid such as a halide, the anhydride or a mixed anhydrides, with a cephalosporin of the general formula:

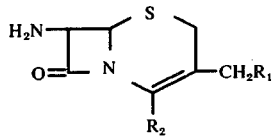

wherein $R_1$ and $R_2$ are as hereinbefore defined.

When the acid of general formula II is used and when $R_2$ in the reactant of general formula III represents the carboxy radical, it is preferable first to protect the acid function of the cephalosporin of general formula III by means of a group which can be easily eliminated after the reaction such as the t-butyl radical. The condensation is generally carried out in an organic solvent, for example dimethylformamide, in the presence of a condensation agent, for example dicyclohexylcarbodiimide, at a temperature between 0° and 40° C., and then the group which protects the acid function of the cephalosporin is eliminated, for example by scission in an acid medium.

When the acid of general formula II is used in the form of a halide (preferably chloride), the anhydride or a mixed anhydride, protection of the acid function of the cephalosporin of general formula III is unnecessary. The condensation is generally carried out in an organic solvent, for example, chloroform, in the presence of an acid-binding agent such as a nitrogen-containing organic base, for example pyridine or triethylamine, or in an aqueous-organic medium, for example aqueous acetone, in the presence of an alkaline condensation agent, for example sodium bicarbonate.

The compound of general formula III wherein $R_1$ represents a hydrogen atom and $R_2$ is the carboxy radical is 7-amino-3-desacetoxycephalosporanic acid (or 7-ADCA) which can be prepared either from a penicillin, for example in accordance with the process described in the specification of British Patent No. 1270633 granted to Eli Lilly and Company on an application filed Mar. 18, 1970, or by desacetoxylation of the compound of general formula III wherein $R_1$ represents the acetoxy radical and $R_2$ represents the carboxy radical, for example in accordance with the process described in the specifications of British Patent 1366211 granted to Smith, Kline and French laboratories on an application filed Feb. 22, 1972.

The compound of general formula III wherein $R_1$ represents the acetoxy radical and $R_2$ is the carboxy radical is 7-aminocephalosporanic acid (or 7-ACA) which can be prepared, for example, in accordance with the procedures described in the specification of British Patent No. 948858 granted to Eli Lilly & Company on an application filed Mar. 30, 1962 and in the specification of U.S. Pat. No. 3239394 granted to R. B. Walton and assigned to Merck and Co.

The compounds of general formula III wherein $R_1$ represents a (5-methyl-1,3,4-thiadiazol-2-yl)thio or (1-methyl-1,2,3,4-tetrazol-5-yl)thio radical and $R_2$ represents a carboxy radical, or alternatively $R_1$ $_1$ represents a pyridinio radical and $R_2$ represents the carboxylate ion, can be prepared by the action of 5-methyl-2-thioxo-1,3,4-thiadiazoline, 1-methyl-5-thioxo-1,2,3,4-tetrazoline, or pyridine on a compound of general formula III wherein $R_1$ represents the acetoxy radical and $R_2$ represents the carboxy radical. The reaction is generally carried out by heating the reactants in an alkalne aqueous medium at a temperature between 40° and 80° C. and optionally, more particularly when $R_1$ represents a pyridinio radical, in the presence of an activator such as an alkali metal iodide or thiocyanate.

The acetic acid derivatives of general formula III can be prepared by saponification of corresponding methyl or ethyl esters.

The methyl or ethyl ester of the acids of general formula II wherein A represents an oxygen or sulphur atom and $A_1$ represents a sulphur atom can be prepared by the action of methyl or ethyl γ-bromoacetoacetate on 2-mercaptoethanol or ethanedithiol, depending on the particular case.

The methyl or ethyl ester of the acid of general formula II wherein A represents a sulphur atom and $A_1$ represents an oxygen atom can be prepared by the action of methyl or ethyl 3-bromo-3-formylpropionate on 2-mercaptoethanol.

According to another feature of the invention, the cephalosporin derivatives of general formula I wherein the symbols A and $A_1$ are as hereinbefore defined, the symbol $R_1$ represents the (5-methyl-1,3,4-thiadiazol-2-yl)thio or (1-methyl-1,2,3,4-tetrozol-5-yl)thio radical and the symbol $R_2$ represents the carboxy radical, or alternatively the symbol $R_1$ represents the pyridinio radical and the radical $R_2$ represents the carboxylate ion, are also prepared by the process which comprises reacting 5-methyl-2-thioxo-1,3,4-thiadiazoline, 1-methyl-5-thioxo-1,2,3,4-tetrazoline or pyridine with a compound of general formula I wherein A and $A_1$ are as hereinbefore defined, $R_1$ represents the acetoxy radical and $R_2$ represents the carboxy radical. The reaction is generally carried out by heating the reactants in an alkaline aqueous medium at a temperature between 40° and 80° C. and optionally, more particularly when $R_1$ represents a pyridinio radical, in the presence of an activator such as an alkali metal iodide or thiocyanate.

The new cephalosporin derivatives of the present invention obtained by the aforementioned processes can optionally be purified by physical methods such as chromatography or crystallisation or by chemical methods such as the formation of an ester, purification of the latter and saponification.

The cephalosporin derivatives of general formula I wherein $R_2$ represents the carboxy radical can be converted into metal salts or addition salts with nitrogeneous bases by application of methods known per se. Thus, these salts can be prepared by the action of an alkali metal or alkaline earth metal base, ammonia or amine on an acid of general formula I in a suitable solvent such as an alcohol, an ether, a ketone or water, or by means of an exchange reaction with a salt of an organic acid. The salt formed is precipitated, if necessary after concentration of the solution, and is separated by filtration or decantation.

The new cephalosporin derivatives of general formula I and salts thereof possess particularly valuable antibacterial properties. They manifest noteworthy activity in vitro and in vivo against Gram-positive and Gram-negative microorganisms.

In vitro, the compounds have proved active at concentrations of between 0.01 and 50 $\mu$g./cc. against staphylococcus strains sensitive to penicillin G *staphylococcus aureus* 209 P and *Staphylococcus aureus* Smith) and at concentrations of between 0.1 and 50 $\mu$g./cc. against staphylococcus strains resistant to penicillin G (*Staphylococcus aureus* MB 9) or against Escherichia coli, Monod strain.

In vivo, the compounds have proved active against experimental infections in mice caused by *Staphylococcus aureus* Smith (sensitive to penicillin G) at doses of between 0.1 and 10 mg./kg. animal body weight per day administered orally, and at doses of between 0.01 and 10 mg./kg. animal body weight per day administered subcutaneously, or caused by *Staphylococcus aureus* MB 9 (resistant to penicillin G) at doses of between 10 and 300 mg./kg. animal body weight administered subcutaneously, or caused by Escherichia coli at doses of between 1 and 100 mg./kg. animal body weight per day administered subcutaneously, or between 10 and 500 mg./kg. animal body weight per day administered orally.

For therapeutic use, the cephalosporin derivatives of general formula I may be used as such or, when $R_2$ represents the carboxy radical, in the form of pharmaceutically-acceptable salts, i.e. salts which are non-toxic to the animal organism in therapeutic doses of the salts, such as alkali metal (for example, sodium, potassium or lithium), alkaline earth metal ammonium and amine salts. Of outstanding interest are 2-carboxy-7-[(5,6-dihydro-1,4-dithiin-2-yl)acetamido]-3-[(1-methyl-1,2,3,4-tetrazol-5-yl)thiomethyl]-8-oxo-5-thia-1-aza-bicyclo[4,2,0]oct-2-ene and 2-carboxy-7-[(5,6-dihydro-1,4-dithiin-2-yl)acetamido]-3-[(5-methyl-1,3,4-thiadiazol-2-yl)thiomethyl]-8-oxo-5-thia-1-aza-bicyclo[4,2,0]oct-2-ene and salts thereof, and 2-carboxylato-7-[(5,6-dihydro-1,4-dithiin-2-yl)acetamido]-8-oxo-3-(1-pyridinio-methyl)-5-thia-1-aza-bicyclo[4,2,0]oct-2-ene.

The following Examples illustrate the preparation of new cephalosporin derivatives of the present invention.

EXAMPLE 1

Thionyl chloride (14.9 g.) and dimethylformamide (3 drops) are added to a solution of (5,6-dihydro-1,4-dithiin-2-yl)acetic acid (11 g.) in benzene (250 cc.). The mixture is heated under reflux until gas ceases to be evolved and is then concentrated to dryness under reduced pressure (20 mm.Hg). Twice, benzene (75 cc.) is added and the resulting mixture is concentrated to dryness under reduced pressure (20 mm.Hg), in order to remove the remaining thionyl chloride.

The residue is dissolved in chloroform (100 cc.) and the solution obtained is added, over the coarse of 1 hour and whilst keeping the temperature at 0° C., to a solution of 7-aminocephalosporanic acid (17 g.) and triethylamine (12.75 g.) in chloroform (250 cc.). The mixture is left for two hours at a temperature of about 20° C. and is then concentrated to dryness under reduced pressure (20 mm.Hg). The residue is taken up in water (300 cc.), and a saturated aqueous solution of sodium bicarbonate (50 cc.) and ethyl acetate (300 cc.) are added; the mixture is stirred and is then filtered through "Supercel". The organic phase is separated and discarded. Ethyl acetate (a further 300 cc.) is added to the aqueous phase and the resulting mixture is acidified, with stirring, to pH 1.5 by addition of 4N hydrochloric acid. The organic phase is separated and the aqueous phase extracted three times with ethyl acetate (total 600 cc.). The organic extracts are combined, dried over sodium sulphate, treated with decolourizing charcoal, and concentrated to dryness under reduced pressure (20 mm.Hg); a residue (23.6 g.) is obtained and is taken up in ethyl acetate (1.5 liters). A 0.6N solution (83 cc.) of sodium 2-ethylhexanoate in butanol is added, and a product precipitates. The mixture is stirred for 1 hour, and the solid is filtered off, washed with diisopropyl ether (100 cc.) and dried under reduced pressure (20 mm.Hg). The sodium salt of 3-acetoxymethyl-2-carboxy-7-[(5,6-dihydro-1,4-dithiin-2-yl)acetamido]-8-oxo-5-thia-1aza-bicyclo[4,2,0]oct-2-ene (17.1 g.) is thus obtained.
$[\alpha]_D^{20} = +110° \pm 2°$; $[\alpha]_{436}^{20} = +226° \pm 3°$ (c = 1,in water).

The (5,6-dihydro-1,4-dithiin-2-yl)acetic acid employed as starting material is prepared in the following way:

10N Sodium hydroxide solution (71.4 cc.) is added to a solution of ethyl (5,6-dihydro-1,4-dithiin-2-yl)acetate (121.3 g.) in ethanol (800 cc.). The reaction mixture is heated for 3 hours at about 50° C. After evaporating the solvent under reduced pressure (25 mm.Hg), the residue is dissolved in distilled water (500 cc.). The alkaline aqueous solution is washed twice with ether (total 100 cc.), treated with decolourizing charcoal (0.2 g.), filtered and then acidified with excess hydrochloric acid ($d = 1.19$). The oil which separates out is extracted three times with diethyl ether (total 450 cc.). The combined ether solutions are washed three times with distilled water (total 300 cc.), dried over anhydrous magnesium sulphate and evaporated. The residue (102.2 g.) is dissolved in boiling diisopropyl ether (150 cc.) and then petroleum ether (b.p. 40°–60° C.) (50 cc.) is added. After 3 hours at 2° C., the crystals which have appeared are filtered off, washed twice with ice-cold diisopropyl ether (total 60 cc.) and dried under reduced pressure (25 mm.Hg) to give (5,6-dihydro-1,4-dithiin-2-yl)acetic acid (82.2 g.) melting at 82° C.

Ethyl (5,6-dihydro-1,4-dithiin-2-yl)acetate is prepared in the following way:

A solution of ethanedithiol (94.0 g.) in anhydrous ethanol (300 cc.) is added, at about 10° C. and over the course of 15 minutes, to a solution of sodium ethoxide (68.0 g.) in anhydrous ethanol (700 cc.), and then ethyl γ-bromoacetoacetate (209.0 g.) is added at about 45°–50° C. over the course of 30 minutes. The reaction mixture is stirred for 2.5 hours at a temperature of about 25° C. After filtration, the solvent is evaporated at about 70° C. under reduced pressure (25 cc.Hg). The residue is dissolved in anhydrous toluene (1,000 cc.); after filtration followed by the addition of toluene-p-sulphonic acid monohydrate (2.0 g.), the reaction mixture is heated under reflux until complete dehydration has taken place (the water formed is removed in a Dean-Stark apparatus). After cooling, the toluene solution is washed twice with a 5% aqueous solution of sodium bicarbonate (total 200 cc.) and twice with distilled water (total 400 cc.), dried over anhydrous magnesium sulphate and evaporated under reduced pressure (25 mm.Hg). The residue (197.5 g.) is distilled. Ethyl (5,6-dihydro-1,4-dithiin-2-yl)acetate (100.7 g.), b.p. 125°–128° C./0.1 mm.Hg, is obtained.

Ethyl γ-bromoacetoacetate can be prepared according to A. Burger and G. E. Ullyot, J. Org. Chem. 12, 346 (1947).

EXAMPLE 2

3-Acetoxymethyl-7-amino-2(t-butoxycarbonyl)-8-oxo-5-thia-1-aza-bicyclo[4,2,0]oct-2-ene (11.2 g.) and dicyclohexylcarbodiimide (7.8 g.) are added to a solution of (5,6-dihydro-1,4-dithiin-2-yl)acetic acid (6 g.) in dimethylformamide (50 cc.). The reagents are left in contact for 5 hours, with stirring, at a temperature of about 20° C. and then the solid is filtered off. The filtrate is taken up in ethyl acetate (300 cc.) and is washed with an aqueous solution of sodium bicarbonate, N hydrochloric acid and then with water. After drying over sodium sulphate, it is treated with decolourizing charcoal and concentrated to dryness under reduced pressure (20 mm.Hg). A residue (20 g.) is obtained and is chromatographed on silica (330 g.). Elution is effected using a mixture (10 liters) of ethyl acetate and cyclohexane (1–3 by volume), and the eluates are concentrated to dryness under reduced pressure (20 mm.Hg). 3-Acetoxymethyl-2-(t-butoxycarbonyl)-7-[(5,6-dihydro-1,4-dithiin-2-yl)acetamido]-8-oxo-5-thia-1-aza-bicyclo-[4,2,0]oct-2-ene (10.3 g.), melting at 80° C., is thus obtained.

3-Acetoxymethyl-2-(t-butoxycarbonyl)-7-[(5,6-dihydro-1,4-dithiin-2-yl)acetamido]-8-oxo-5-thia-1-aza-bicyclo[4,2,0]oct-2-ene (9.6 g.) is dissolved in trifluoroacetic acid (100 cc.). The reagents are left in contact for 1 hour, whilst cooling with an ice-water bath. The mixture is concentrated to dryness under reduced pressure (1 mm.Hg), ethyl acetate (150 cc.) is added and the resulting mixture is again concentrated to dryness under reduced pressure.

The residue is taken up in an aqueous solution of sodium bicarbonate and washed with ethyl acetate. The aqueous phase is acidified to pH 1.2 using 4N hydrochloric acid in the presence of ethyl acetate. The organic phase is isolated and the aqueous phase is extracted with ethyl acetate. The combined organic extracts are filtered through "Supercel", dried over magnesium sulphate and concentrated to dryness under reduced pressure (20 mm.Hg). The residue is washed with diisopropyl ether to give 3-acetoxymethyl-2-carboxy-7-[(5,6-dihydro-1,4-dithiin-2-yl)acetamido]-8-oxo-5-thia-1-aza-bicyclo[4,2,0]oct-2-ene (3.5 g.).
$[\alpha]_D^{20} = +70.4° \pm 1.5°$ ($c = 1$, dimethylformamide).

3-Acetoxymethyl-7-amino-2-(t-butoxycarbonyl)-8-oxo-5-thia-1-aza-bicyclo[4,2,0]oct-2-ene can be prepared according to R. J. Stedman, J. Med. Chem., 9, 444 (1966).

EXAMPLE 3

Thionyl chloride (3 cc.) is added to a solution of (5,6-dihydro-1,4-dithiin-2-yl)acetic acid (3.10 g.) in benzene (60 cc.), and the mixture is heated under reflux until gas ceases to be evolved. The reaction mixture is then concentrated to dryness under reduced pressure (20 mm.Hg). A brown oil is obtained and is dissolved in chloroform (60 cc.). The solution is added dropwise, over the course of one hour, to a suspension of 7-aminodesacetoxycephalosporanic acid (4.28 g.) in chloroform (50 cc.) and triethylamine (5.5 cc.) kept at 5° C. The mixture is stirred for a further 45 minutes at a temperature of about 20° C. and is concentrated to dryness under reduced pressure (20 mm.Hg). The residue is taken up in water (100 cc.) and ethyl acetate (100 cc.) and the aqueous phase is brought to pH 8.5 by addition of triethylamine. The organic phase is separated by decantation. Ethyl acetate (300 cc.) is added to the aqueous phase and 4N hydrochloric acid is added until the pH is 2. The organic phase is separated, the aqueous phase is washed with ethyl acetate (100 cc.), and the organic phases are combined, dried over magnesium sulphate, treated with decolourizing charcoal and concentrated to 50 cc. under reduced pressure (20 mm.Hg). After cooling to about 0° C., the solid is filtered off and washed with ethyl acetate (2 × 20 cc.). 2-Carboxy-7-[(5,6-dihydro-1,4-dithiin-2-yl)acetamido]-3-methyl-8-oxo-5-thia-1-aza-bicyclo[4,2,0]oct-2-ene (2.6 g.) is obtained in the form of a light beige powder.
$[\alpha]_D^{20} = +114.6° \pm 2°$ ($c = 1$; dimethylformamide).

7-Aminodesacetoxycephalosporanic acid can be prepared according to R. J. Stedman, K. Swered and J. R. E. Hoover, J. Med. Chem., 7, 117 (1964).

EXAMPLE 4

Thionyl chloride (8.7 g.) is added to a solution of (5,6-dihydro-1,4-dithiin-2-yl)acetic acid (6.45 g.) in benzene (120 cc.). The mixture is heated under reflux until gas ceases to be evolved and is then concentrated to dryness under reduced pressure (20 mm.Hg). The brown oil thus obtained is dissolved in acetone (50 cc.) and the resulting solution is added dropwise, over the course of one hour, to a solution of 7-amino-2-carboxy-3-[(1-methyl-1,2,3,4-tetrazol-5-yl)thiomethyl]-8-oxo-5-thia-1-aza-bicyclo[4,2,0]oct-2-ene (12 g.) and sodium bicarbonate (7.35 g.) in water (200 cc.) and acetone (100 cc.) kept at 3° C. Stirring is continued for a further hour at 3° C. and then for 2 hours at about 20° C. The mixture is concentrated to dryness under reduced pressure (20 mm.Hg), water (150 cc.) is added and the slight amount of insoluble matter is filtered off. The solution is washed twice with ethyl acetate (300 cc.) and brought to pH 2.2 by addition of 4N hydrochloric acid in the presence of ethyl acetate (300 cc.). The solution is filtered through "Supercel" and decanted, and the aqueous phase is extracted with ethyl acetate (300 cc.). The organic phases are combined and washed with water (200 cc.), dried over magnesium sulphate and treated with decolourizing charcoal. The mixture is filtered and the filtrate is concentrated to a volume of 100 cc. Diethyl ether (700 cc.) is then added and the mixture is cooled to about 0° C.; the resulting precipitate is filtered off and washed with diethyl ether (100 cc.). 2-Carboxy-7-[(5,6-dihydro-1,4-dithiin-2-yl)-acetamido]-3-[(1-methyl-1,2,3,4-tetrazol-5-yl)thiomethyl]-8-oxo-5-thia-1-aza-bicyclo[4,2,0]oct-2-ene (4.4 g.) is obtained in the form of a cream powder.

$[\alpha]_D^{20} = -71.1° \pm 1.5°$ ($c = 1$, dimethylformamide).

7-Amino-2-carboxy-3-[(1-methyl-1, 2, 3, 4-tetrazol-5-yl)thiomethyl]-8-oxo-5-thia-1-aza-bicyclo-[4,2,0]oct-2-ene can be prepared according to the method described in U. S. Pat. No. 3,516,997.

EXAMPLE 5

Thionyl chloride (12.4 g.) and dimethylformamide (5 drops) are added to a solution of (5,6-dihydro-1,4-oxathiin-2-yl)acetic acid (8.3 g.) in anhydrous diethyl ether (50 cc.). The mixture is heated under reflux until gas ceases to be evolved and is then concentrated to dryness under reduced pressure (20 mm.Hg). Three times, benzene (70 cc.) is added and the resulting mixture is concentrated to dryness under reduced pressure (20 mm.Hg), in order to remove the remaining thionyl chloride.

The residue is dissolved in chloroform (80 cc.); the solution obtained is added over the course of one hour, and whilst keeping the temperature at −10° C., to a solution of 7-aminocephalosporanic acid (14.3 g.) and triethylamine (10.6 g.) in chloroform (220 cc.). The mixture is left for 15 hours at a temperature of about +4° C. and is then concentrated to dryness under reduced pressure (20 mm.Hg). The residue is taken up in water (300 cc.), and a saturated aqueous solution of sodium bicarbonate (50 cc.) and ethyl acetate (300 cc.) are added; the resulting mixture is stirred and then filtered through "Supercel". The organic phase is separated and discarded. Ethyl acetate (400 cc.) is added to the aqueous phase and the resulting mixture is acidified, with stirring, to pH 2 by addition of 4N hydrochloric acid. The mixture is stirred and then filtered through "Supercel", and finally the organic phase is isolated by decantation. The organic extracts are washed with water (4 × 250 cc.), dried over sodium sulphate, treated with decolourizing charcoal, and concentrated to dryness under reduced pressure (20 mm.Hg); a residue (14.8 g.) is obtained and is taken up in ethyl acetate (50 cc.). After 30 minutes at 2° C., the solid which has precipitated is filtered off, washed twice with ethyl acetate (15 cc.) and then twice with diisopropyl ether (15 cc.) and dried under reduced pressure (0.5 mm.Hg). 3-Acetoxymethyl-2-carboxy-7-[(5,6-dihydro-1,4-oxathiin-2-yl)acetamido]-8-oxo-5-thia-1-aza-bicyclo[4,2,0]oct-2-ene (6.4 g.), which melts with decomposition at 190°–191° C., is obtained.

$[\alpha]_D^{20} = + 67.8° \pm 1.5°$ ($c = 1$, dimethylformamide).

The (5,6-dihydro-1,4-oxathiin-2-yl)acetic acid employed as starting material can be prepared in the following way:

A solution of sodium hydroxide (5 g.) in water (30 cc.) is added to a solution of ethyl (5,6-dihydro-1,4-oxathiin-2-yl)acetate (20 g.) in ethanol (55 cc.). The reaction mixture is heated for one hour at 50° C. and is then allowed to return to about 20° C., and ethanol is added (100 cc.). After one hour at +2° C., the crystals which have appeared are filtered off and washed twice with ethanol (25 cc.). The crystalline compound obtained is dried under reduced pressure (0.5 mm.Hg) over potassium hydroxide. The sodium salt of (5,6-dihydro-1,4-oxathiin- 2-yl)-acetic acid (15.2 g.), melting at 248° C., is obtained.

The aforesaid sodium salt is dissolved in distilled water (50 cc.); the solution is acidified by addition of 4N hydrochloric acid and is then extracted twice with diethyl ether (150 cc.). The ether extracts are combined, washed twice with water (100 cc.), dried over sodium sulphate and treated with decolourizing charcoal. After concentration to dryness under reduced pressure (20 mm.Hg), (5,6-dihydro-1,4-oxathiin-2-yl)acetic acid (13 g.) is obtained in the form of an oil.

Ethyl (5,6-dihydro-1,4-oxathiin-21)acetate can be prepared in the following way:

A solution of 2-mercaptoethanol (58.5 g.) in anhydrous ethanol (220 cc.) is added, at about 10° C. and over the course of one hour, to a solution of sodium ethoxide in ethanol [prepared by reacting sodium (17.2 g.) with anhydrous ethanol (570 cc.)]. After having heated the reaction mixture to 45°–50° C., ethyl γ-bromoacetoacetate (157 g.) is added over the course of 45 minutes, and then the reaction mixture is stirred for 2 hours at a temperature of about 25° C. After filtration, the solvent is evaporated at about 50° C. under reduced pressure (20 mm.Hg). The residue is dissolved in anhydrous toluene (1,000 cc.) and, after filtration of the resulting solution, toluene-p-sulphonic acid monohydrate (1.5 g.) is added. The reaction mixture is heated under reflux until complete dehydration has taken place (the water formed being removed in a Dean-Stark apparatus) and then toluene (200 cc.) is distilled. After cooling, the toluene solution is filtered and washed twice with a saturated aqueous solution of sodium bicarbonate (200 cc.) and then with water (2 × 200 cc.); it is then dried over sodium sulphate, treated with decolourizing charcoal, filtered and evaporated under reduced pressure (20 mm.Hg). A residue (131.9 g.) is obtained and is chromatographed on alumina (550 g.). Elution is effected using a mixture (2.5 liters) of ethyl acetate and cyclohexane (1–19 by volume) and the eluates are concentrated to dryness under reduced pressure (20 mm.Hg). Ethyl (5,6-dihydro-1,4-oxathiin-2-yl)acetate (75.7 g.) is obtained in the form of an oil.

EXAMPLE 6

Thionyl chloride (13.2 g.) and dimethylformamide (5 drops) are added to a solution of (5,6-dihydro-1,4-oxathiin-3-yl)acetic acid (8.9 g.) in anhydrous diethyl ether (90 cc.). The mixture is heated under reflux until gas ceases to be evolved and is then concentrated to dryness under reduced pressure (20 mm.Hg). Twice, chloroform (50 cc.) is added and the resulting mixture is concentrated to dryness under reduced pressure (20 mm.Hg), in order to remove the remaining thionyl chloride.

The residue is dissolved in chloroform (90 cc.); the solution obtained is added, over the course of one hour and whilst keeping the temperature at −10° C., to a solution of 7-aminocephalosporanic acid (15.1 g.) and triethylamine (11.2 g.) in chloroform (240 cc.). The mixture is left for 15 hours at a temperature of about +4° C. and is then concentrated to dryness under reduced pressure (20 mm.Hg). The residue is taken up in water (250 cc.) and is brought to pH 7.5 by addition of a saturated aqueous solution of sodium bicarbonate. The solution obtained is washed with ethyl acetate (2 × 250 cc.); the organic layers are isolated and discarded. Ethyl acetate (a further 300 cc.) is added to the aqueous phase which is then acidified, with stirring, to pH 2 by addition of 4N hydrochloric acid. The mixture is filtered through "Supercel". The organic phase is separated by decantation, washed with water (2 × 100 cc.), dried over sodium sulphate and treated with decolourizing charcoal. After concentration to dryness under reduced pressure (20 mm.Hg), a residue (16 g.) is obtained and is taken up in ethyl acetate (50 cc.). Diisopropyl ether (500 cc.) is added, with stirring, to the solution thus obtained. The mixture is stirred for one hour and then the solid which has appeared is filtered off. The solid is washed twice with diisopropyl ether (total 200 cc.), and then dried under reduced pressure (0.5 mm.Hg) to give 3-acetoxymethyl-2-carboxy-7-[(5,6-dihydro-1,4-oxathiin-3-yl )acetamido]-8-oxo-5-thia-1-aza-bicyclo [4,2,0]oct-2-ene (8.1 g.). $[\alpha]_D^{20} = +85.7° \pm 1.5$ ($c = 0.95$, dimethylformamide).

(5,6-Dihydro-1,4-oxathiin-3-yl )acetic acid employed as starting material can be prepared in the following way:

A solution of sodium hydroxide (3.2 g.) in water (18 cc.) is added to a solution of ethyl (5,6-dihydro-1,4-oxathiin-3-yl )acetate (13.4 g.) in ethanol (134 cc.). The reaction mixture is heated for one hour at 60° C. and is then concentrated to dryness under reduced pressure (20 mm.Hg). The resulting residue is taken up in water (250 cc.), and the mixture extracted with diethyl ether (200 cc.), decanted and the ether phase is discarded. The aqueous phase is acidified to pH 1 by addition of 4N hydrochloric acid and is then extracted three times with diethyl ether (total 600 cc.). The ether fractions are combined, washed twice with water (total 200 cc.), dried over sodium sulphate and treated with decolourizing charcoal. After filtration and concentration to dryness under reduced pressure (20 mm.Hg), (5,6-dihydro-1,4-oxathiin-3-yl )acetic acid (8.9 g.) is obtained in the form of an oil which is used as it is.

Ethyl (5,6-dihydro-1,4-oxathiin-3-yl )acetate can be prepared in the following way:

A solution of 2-mercaptoethanol (38.2 g.) in anhydrous ethanol (146 cc.) is added, at about 10° C. and over the course of one hour, to a solution of sodium ethoxide in ethanol [prepared by reacting sodium (11.2 g.) with anhydrous ethanol (350 cc.)]. After heating the reaction mixture to a temperature of 45°–f 50° C., ethyl 3-bromo-3-formylpropionate (102.8 g.) is added over the course of 20 minutes. The reaction mixture is stirred for 15 hours at a temperature of about 25° C. After filtration, the solvent is evaporated at about 50° C. under reduced pressure (20 mm.Hg). The residue is dissolved in anhydrous toluene (500 cc.); the solution is filtered and toluene-p-sulphonic acid monohydrate (1.5 g.) is then added. The reaction mixture is heated under reflux until complete dehydration has taken place (the water formed being removed in a Dean-Stark apparatus) and then the solvent is evaporated at about 50° C. under reduced pressure (20 mm.Hg). The residue is taken up in diethyl ether (700 cc.); some insoluble matter appears and is removed by filtration through "Supercel". The ether solution is washed three times with water (total 600 cc.), then dried over sodium sulphate, treated with decolourizing charcoal and filtered. The solution is concentrated to dryness under reduced pressure (20 mm.Hg); a residue (65 g.) is obtained and is chromatographed on alumina (600 g.). Elution is effected using a mixture (2.6 liters) of ethyl acetate and cyclohexane (1-19 by volume). After concentration to dryness under reduced pressure (20 mm.Hg), ethyl (5,6-dihydro-1,4-oxathiin-3-yl )acetate (16.8 g.) is obtained in the form of an oil.

Ethyl 3-bromo-3-formylpropionate can be prepared according to M. Aeberli and M. Erlenmeyer, Helv. Chim. Acta. 33, 503 (1950).

EXAMPLE 7

The sodium salt of 3 -acetoxymethyl-2-carboxy-7-[(5,6-dihydro-1,4-dithiin-2-yl )acetamido]-8-oxo-5-thia-1-aza-bicyclo [4,2,0]oct-2-ene (10 g.) is dissolved in distilled water (200 cc.). Sodium bicarbonate (2.25 g.) followed by 2-methyl-5-thioxo-1,3,4-thiadiazoline (3.54 g.) are added to the solution and the mixture is heated with stirring at 60° C. for 16 hours. After cooling, the reaction mixture is washed with ethyl acetate (200 cc.). The pH of the mixture is brought to 6.5 by addition of 4N hydrochloric acid and then the mixture is washed again with ethyl acetate (200 cc.). The mixture is acidified to pH 2 by addition of 4N hydrochloric acid in the presence of ethyl acetate (200 cc.). After decanting the organic phase, the aqueous phase is extracted twice with ethyl acetate (total 200 cc.). The organic extracts are combined, washed three times with water (total 500 cc.), dried over sodium sulphate, treated with decolourizing charcoal, filtered and then concentrated to dryness under reduced pressure (20 mm.Hg). The solid residue obtained is taken up in diisopropyl ether (200 cc.), filtered off and then dried under reduced pressure (2 mm.Hg). 2-Carboxy-7-[(5,6-dihydro-1,4-dithiin-2-yl )acetamido]-3-[(5-methyl-1,3,4-thiadiazol-2-yl )thiomethyl]-8-oxo-5-thia-1-aza-bicyclo[4,2,0]oct-2-ene (6 g.), melting at 170° C., is thus obtained. $[\alpha]_D^{20} = -70° \pm 1°$ ($c = 1$, dimethylformamide).

2-Methyl-5-thioxo-1,3,4-thiadiazoline can be prepared according to U.S. Pat. No. 3,073,731.

EXAMPLE 8

3-Acetoxymethyl-2-carboxy-7-[(5,6-dihydro-1,4-dithiin-2-yl )acetamido]-8-oxo-5-thia-1-aza-bicyclo[4,2,0]- oct-2-ene (16.4 g.), sodium bicarbonate (3.75 g.) and 1-methyl-5-thioxo-1,2,3,4-tetrazoline (5.05 g.) are added to a buffer solution (250 cc.) at pH 6.4, and the solution obtained is heated at 60° C. for 6 hours. After cooling, a saturated aqueous solution of sodium bicarbonate (50 cc.) is added and the resulting mixture is washed with ethyl acetate (300 cc.); the aqueous phase is then treated with decolourizing charcoal and is brought to pH 2 by addition of 4N hydrochloric acid in the presence of ethyl acetate (250 cc.). The ethyl acetate is removed by decantation and the aqueous phase is washed with ethyl acetate (300 cc.). The combined organic extracts are dried over magnesium sulphate, treated with decolourizing charcoal and filtered.

In order to purify the cephalosporin derivative, diphenyldiazomethane (8.4 g.) is added to the solution obtained and the mixture is stirred at a temperature of about 20° C. for 16 hours. The mixture is concentrated to dryness under reduced pressure (20 mm.Hg) and the residue (18.8 g.) is chromatographed on silica gel (200 g.), eluting with a mixture of ethyl acetate and cyclohexane (50-50 by volume). On evaporating the solvent, 7-[(5,6-dihydro-1,4-dithiin-2-yl )acetamido]-2-diphenylmethoxy-carbonyl-3-[(1-methyl-1,2,3,4-tetrazol-5-yl )thiomethyl]-8-oxo-5-thia-1-aza-bicyclo[4,2,0]oct-2-ene (7.6 g.) is obtained in the form of a lacquer. The diphenylmethyl ester (7.5 g.) is dissolved in anisole (25 cc.) and trifluoroacetic acid (20 cc.) and the solution is kept at about 20° C. for 15 minutes with stirring. The mixture is concentrated to dryness under reduced pressure (1 mm.Hg) and then ethyl acetate (20 cc.) is added, followed by a saturated aqueous solution of sodium bicarbonate until the pH is 8. The aqueous phase is separated by decantation, washed with ethyl acetate (100 cc.), treated with decolourizing charcoal, filtered and acidified to pH 2 by addition of 4N hydrochloric acid in the presence of ethyl acetate (400 cc.). The organic phase is dried over sodium sulphate, filtered and concentrated to dryness under reduced pressure (20 mm.Hg). 2-Carboxy-7-[(5,6-dihydro-1,4-dithiin-2-yl )acetamido]-3-[(1-methyl-1,2,3,4-tetrazol-5-yl )thiomethyl]-8-oxo-5-thia-1-aza-bicyclo[4,2,0]oct-2-ene (4.5 g.) is obtained.

1-Methyl-5-thioxo-1,2,3,4-tetrazoline can be prepared according to R. Stolle and Fr. Henke-Stark, J. Prakt. Chem., 124, 261 (1930).

EXAMPLE 9

Water (47 cc.) and pyridine (16.1 cc.) are added to the sodium salt of 3-acetoxymethyl-2-carboxy-7-[(5,6-dihydro-1,4-dithiin-2-yl )acetamido]-8-oxo-5-thia-1-aza- bicyclo[4,2,0]oct-2-ene (45.2 g.) and potassium thiocyanate (194 g.). After stirring, a homogeneous syrupy mixture is obtained, the pH of which is adjusted to 6.5 by addition of concentrated phosphoric acid. The mixture is heated at 60° C. for 5 hours. After cooling, the reaction mixture is diluted with distilled water (1 liter) and is washed three times with chloroform (total 800 cc.). The last traces of chloroform in the aqueous phase are removed by distillation under reduced pressure (20 mm.Hg) and the resulting solution is then treated with decolourizing charcoal, filtered through "Supercel" and cooled by means of an ice-water bath. The solution is then acidified to pH 2 by addition of 4 N hydrochloric acid whilst keeping the temperature below 5° C.; a product precipitates. The mixture is stirred for one hour whilst continuing to cool it with a mixture of ice and water, and is then washed twice by decantation with ice-water (1 liter). The precipitate is filtered off and is washed three times with ice-water (total 2 liters). The solid obtained is suspended in water (120 cc.) and a 25% solution of "Amberlite LA 2" in methyl isobutyl ketone (120 cc.) is added. The mixture is stirred until the solid has dissolved completely, and then the organic phase is decanted and discarded. The aqueous phase is extracted twice with a 25% solution of "Amberlite LA 2" in methyl isobutyl ketone (total 240 cc.), then with ethyl acetate (300 cc.) and finally three times with diethyl ether (total 300 cc.). The water is evaporated under reduced pressure (20 mm.Hg) at 40° C. An oil is obtained which is triturated in acetone (800 cc.). The resulting solid is filtered off, washed three times with acetone (total 300 cc.) and then dried under reduced pressure (0.5 mm.Hg). 2-Carboxylato-7-[(5,6-dihydro-1,4-dithiin-2-yl )acetamido]-8-oxo-3- (1-pyridiniomethyl)-5-thia-1-aza-bicyclo[4,2,0]- oct-2-ene (8.3 g.) is thus obtained.

$[\alpha]_D^{20} = +67.8° \pm 1.3°$ ($c = 1$, water).

EXAMPLE 10

The sodium salt of 3-acetoxymethyl-2-carboxy-7-[(5,6-dihydro-1,4-oxathiin-2-yl )acetamido]-8-oxo-5-thia-1-aza-bicyclo[4,2,0]oct-2-ene (14 g.) is dissolved in distilled water (350 cc.). Sodium bicarbonate (2.69 g.) followed by 2-methyl-5-thioxo-1,3,4-thiadiazoline (4.65 g.) are added to the solution and the reaction mixture is heated with stirring at 60° C. for 6 hours. After cooling, the reaction mixture is washed with ethyl acetate (2 × 150 cc.) and then acidified to pH 2 by addition of 4N hydrochloric acid in the presence of ethyl acetate (350 cc.). After decanting the organic phase, the aqueous phase is extracted twice with ethyl acetate (total 150 cc.). The organic extracts are combined, washed six times with water (total 600 cc.), dried over sodium sulphate, treated with decolourizing charcoal, filtered and then concentrated under reduced pressure (20 mm.Hg) to a final volume of 80 cc. After 30 minutes at 2° C., the solid compound which has formed is filtered off and then washed twice with ethyl acetate (10 cc.) and finally with diisopropyl ether (100 cc.). After drying under reduced pressure (0.5 mm.Hg), 2-carboxy-7-[(5,6-dihydro-1,4-oxathiin-2-yl )acetamido]-3-[(5-methyl-1,3,4-thiadiazol-2-yl )thiomethyl]-8-oxo-5-thia-1-aza-bicyclo[4,2,0]oct-2-ene (7.5 g.) is obtained.

$[\alpha]_D^{20} = -90.7° \pm 1.5°$ ($c = 1$, dimethylformamide).

The sodium salt of 3-acetoxymethyl-2-carboxy-7-[(5,6-dihydro-1,4-oxathiin-2-yl )acetamido]-8-oxo-5-thia-1-aza-bicyclo[4,2,0]oct-2-ene is prepared in the following way:

A 0.6N solution of sodium 2-ethylhexanoate in butanol (325 cc.) is added to a solution of 3-acetoxy-methyl-2-carboxy-7-[(5,6-dihydro-1,4-oxathiin-2-yl )acetamido]-8-oxo-5-thia-1-aza-bicyclo[4,2,0]oct-2-ene (70 g.) in ethyl acetate (2,000 cc.); a product precipitates. The mixture is stirred for one hour and then the solid is filtered off. It is washed three times with ethyl acetate (total 900 cc.), three times with diisopropyl ether (total 750 cc.) and is then dried under reduced pressure (20 mm.Hg). The sodium salt of 3-acetoxymethyl-2-carboxy-7-[(5,6-dihydro-1,4-oxathiin-2-yl )acetamido]-8-oxo-5-thia-1-aza-bicyclo[4,2,0]oct-2-ene (53.8 g.) is thus obtained.

$[\alpha]_D^{20} = +122.1° \pm 1.8°$ ($c = 0.96$; water).

EXAMPLE 11

The sodium salt of 3-acetoxymethyl-2-carboxy-7-[(5,6-dihydro-1,4-oxathiin-2-yl )acetamido]-8-oxo-5-thia-1-aza-bicyclo[4,2,0]oct-2-ene (14 g.) is dissolved in a buffer solution (350 cc.) of pH 6.2, consisting of monopotassium phosphate (47.1 g.), N sodium hydroxide solution (80.9 cc.) and water. Sodium bicarbonate (2.69 g.) followed by 1-methyl-5-thioxo-1,2,3,4-tetrazoline (3.7 g.) are added to the solution and the mixture is heated with stirring at 60° C. for 6 hours. After cooling, the reaction mixture is washed with ethyl acetate (2 × 150 cc.). The mixture is acidified to pH 2 by addition of 4N hydrochloric acid in the presence of ethyl acetate (350 cc). After decanting the organic phase, the aqueous phase is extracted twice with ethyl acetate (total 150 cc.). The organic extracts are combined, washed seven times with water (total 700 cc.), dried over sodium sulphate, treated with decolourizing charcoal, filtered and then concentrated under reduced pressure (20 mm.Hg) until a final volume of 120 cc. is obtained. Diisopropyl ether (120 cc.) is then added with stirring; after precipitation of a solid, the mixture is stirred for one hour and then the solid is filtered off. It is washed twice with diisopropyl ether (total 100 cc.) and then dried under reduced pressure (20 mm.Hg). 2-Carboxy-7-[(5,6-dihydro-1,4-oxathiin-2-yl)acetamido]-3-[(1-methyl-1,2,3,4-tetrazol-5-yl)thiomethyl]-8-oxo-5-thia-1-aza-bicyclo [4,2,0]oct-2-ene, solvated with approximately 10% of ethyl acetate, (4.5 g.) is thus obtained.

The sodium salt of 2-carboxy-7-[(5,6-dihydro-1,4-oxathiin-2-yl)acetamido]-3-[(1-methyl-1,2,3,4-tetrazol-5-yl)thiomethyl]-8-oxo-5-thia-1-aza-bicyclo[4,2,0]oct-2-ene is prepared by dissolving the corresponding acid in a 0.1N aqueous solution of sodium bicarbonate and lyophilizing.

$[\alpha]_D^{20} = +34.9° \pm 0.9°$ ($c = 0.87$, water).

The present invention includes within its scope pharmaceutical compositions comprising, as active ingredient, at least one of the compounds of general formula I or, when $R_2$ in that formula represents the carboxy radical, a pharmaceutically-acceptable salt thereof in association with a pharmaceutical carrier. The invention includes especially such compositions made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy in the treatment of infections of bacterial origin. When administered orally, intramuscularly or intravenously to an adult the doses should generally be between 1g. and 12 g. of active substance per day. In general the physician will decide the posology considered appropriate, taking into account the age, the weight, the degree of infection and other factors intrinsic to the patient being treated.

The following Example illustrates pharmaceutical compositions according to the invention.

EXAMPLE 12

An injectable solution having the following composition is prepared:

| | |
|---|---|
| sodium salt of 3-acetoxymethyl-2-carboxy-7-[5,6-dihydro-1,4-dithiin-2-yl)acetamido]-8-oxo-5-thia-1-aza-bicyclo[4,2,0]oct-2-ene | 262.7 mg. |
| sodium chloride | 1.6 mg. |
| injectable solution | 2 cc. |

We claim:
1. A cephalosporin derivative of the formula:

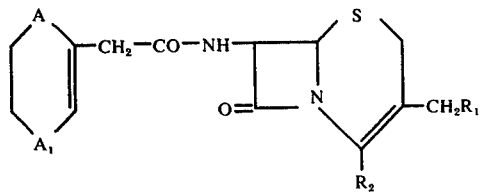

wherein one of A and $A_1$ represents oxygen or sulphur and the other represents sulphur, $R_1$ represents hydrogen, acetoxy, (5-methyl-1,3,4-thiadiazol-2-y)thio or (1-methyl-1,2,3,4-tetrazol-5-yl)thio and $R_2$ represents carboxy, or $R_1$ represents a pyridinio radical and $R_2$ represents the carboxylate ion, and when $R_2$ represents the carboxy radical pharmaceutically-acceptable salts thereof.

2. A cephalosporin derivative according to claim 1 wherein A and $A_1$ each represent sulphur.

3. The cephalosporin derivative according to claim 1 which is 3-acetoxymethyl-2-carboxy-7-[(5,6-dihydro-1,4-dithiin-2-yl) acetamido]-8-oxo-5-thia-1-aza-bicyclo-[4,2,0]oct-2-ene and pharmaceutically-acceptable salts thereof.

4. The cephalosporin derivative according to claim 1 which is 2-carboxy-7-[(5,6-dihydro-1,4-dithiin-2- yl )acetamido]-3-methyl-8-oxo-5-thia-1-aza-bicyclo[4,2,0]-oct-2-ene and pharmaceutically-acceptable salts thereof.

5. The cephalosporin derivative according to claim 1 which is 2-carboxy-7-[(5,6-dihydro-1,4-dithiin-2-yl)acetamido]-3-[(1-methyl-1,2,3,4-tetrazol-5-yl)-thiomethyl]-8-oxo-5-thia-1-aza-bicyclo]4,2,0]oct-2-ene and pharmaceutically-acceptable salts thereof.

6. The cephalosporin derivative according to claim 1 which is 3-acetoxymethyl-2-carboxy-7-[(5,6-dihydro- 1,4-oxathiin-2-yl )acetamido]-8-oxo-5-thia-1-aza-bicyclo-[4,2,0]oct-2-ene and pharmaceutically-acceptable salts thereof.

7. The cephalosporin derivative according to claim 1 which is 3-acetoxymethyl-2-carboxy-7-[(5,6-dihydro-1,4-oxathiin-3-yl )acetamido]-8-oxo-5-thia-1-aza-bicyclo[4,2,0]oct-2-ene and pharmaceutically-acceptable salts thereof.

8. The cephalosporin derivative according to claim 1 which is 2-carboxy-7-[(5,6-dihydro-1,4-dithiin-2-yl ) acetamido]-3-[(5-methyl-1,3,4-thiadiazol-2-yl )thiomethyl]-8-oxo-5-thia-1-aza-bicyclo[4,2,0]oct-2-ene and pharmaceutically-acceptable salts thereof.

9. The cephalosporin derivative according to claim 1 which is 2-carboxylato-7-[(5,6-dihydro-1,4-dithiin-2-yl ) acetamido]-8-oxo-3-(1-pyridinio-methyl)-5-thia-1-aza-bicyclo[4,2,0]oct-2-ene.

10. The cephalosporin derivative according to claim 1 which is 2-carboxy-7-[(5,6-dihydro-1,4-oxathiin-2-yl )acetamido[-3-[(5-methyl-1,3,4-thiadiazol-2-yl )-thiomethyl]-8-oxo-5-thia-1-aza-bicyclo[4,2,0[oct-2-ene and pharmaceutically-acceptable salts thereof.

11. The cephalosporin derivative according to claim 1 which is 2-carboxy-7-[(5,6-dihydro-1,4-oxathiin-2-yl )acetamido]-3-[(1-methyl-1,2,3,4-tetrazol-5-yl )thiomethyl]-8-oxo-5-thia-1-aza-bicyclo[4,2,0]oct-2-ene and pharmaceutically-acceptable salts thereof.

12. Alkali metal, alkaline earth metal, ammonium and pharmaceutically-acceptable amine salts of a cephalosporin derivative as claimed in claim 1 wherein $R_2$ represents the carboxy radical.

* * * * *